(12) United States Patent
Hall et al.

(10) Patent No.: US 6,602,491 B2
(45) Date of Patent: Aug. 5, 2003

(54) COMPOSITION CONTAINING ALKYLHYDROXYBENZOATES

(75) Inventors: Peter John Hall, Merseyside (GB); David Thomas Littlewood, Merseyside (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/225,861

(22) Filed: Aug. 22, 2002

(65) Prior Publication Data

US 2003/0082112 A1 May 1, 2003

(30) Foreign Application Priority Data

Aug. 24, 2001 (EP) .............................. 01307269
Dec. 11, 2001 (EP) .............................. 01310338
Aug. 6, 2002 (EP) .............................. 02255498

(51) Int. Cl.[7] .......................... A61K 7/16; A61K 33/10; A61K 33/00
(52) U.S. Cl. .......................... 424/49; 424/687; 424/717
(58) Field of Search .............................. 424/49–58, 687, 424/717

(56) References Cited

U.S. PATENT DOCUMENTS

| 5,000,942 | A | | 3/1991 | Libin |
| 5,094,841 | A | * | 3/1992 | Fine ............................ 424/52 |
| 5,976,578 | A | * | 11/1999 | Beyerle et al. ............. 424/687 |
| 6,335,005 | B1 | | 1/2002 | Muller et al. |

FOREIGN PATENT DOCUMENTS

| EP | 0 161 898 | | 5/1985 |
| EP | 0161898 | * | 11/1985 |
| EP | 0 523 376 | | 6/1992 |
| WO | 92/18111 | | 10/1992 |
| WO | 98/47477 | | 10/1998 |
| WO | 99/00104 | | 1/1999 |
| WO | 00/09507 | | 2/2000 |
| WO | 00/59401 | | 11/2000 |
| WO | 00/69401 | * | 11/2000 |
| WO | 01/62224 | | 8/2001 |

OTHER PUBLICATIONS

Okada et al HCAPLUS : 642274 : 1999 CA . 132 :191320 Bio Control Science : 4(2): 67–73 (1999) Calorimetric Analysis of Antimicrobial Effect of P hydroxybenzoic Acid Alkyl Esters, 1999.*

Shibasaki HCAPLUS : 95520 : 1969 CA . 70: 95520 Hakko Kogaku Zasshi 47(3): 167–177 (1969) Antimicrobial Activity of Alkyl Esters of P. Hydroxybenzoic Acid (In English), 1969.*

GB Search Report.

* cited by examiner

Primary Examiner—Shep K. Rose
(74) Attorney, Agent, or Firm—Milton L. Honig

(57) ABSTRACT

Oral composition comprising:

(a) an alkyl hydroxybenzoate represented by formula 1

Formula 1:

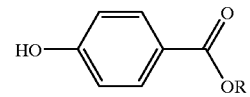

wherein R represents an alkyl group comprising at least five carbon atoms, and (b) said composition having an alkaline pH.

14 Claims, No Drawings

COMPOSITION CONTAINING ALKYLHYDROXYBENZOATES

The present invention relates to a composition comprising an alkyl hydroxybenzoate.

INTRODUCTION

Alkyl hydroxybenzoates (parabens) are known in the art where the alkyl group is methyl. For example, methyl hydroxybenzoate is mentioned, albeit fleetingly, for use in medicinal and oral care preparations as a preservative (WO 00/09507 and WO 00/69401).

In addition, U.S. Pat. No. 5,094,841 (Fine) discloses the use of heptyl paraben as a preservative in an oral care formulation. However, it also states that the preferred preservatives are methyl and propyl paraben and only ever states that they may be included in small amounts (0.1%) to provide a preservative effect.

EP-A2-0 161 898 (Unilever) discloses the use of parabens in oral care, in particular, methyl, ethyl, propyl, isopropyl, butyl, isobutyl, hexyl, heptyl and benzyl parabens.

We have surprisingly found that alkyl esters of para hydroxy benzoic acid can be formulated in an oral care composition with an alkaline pH and contrary to what would have been expected they do not hydrolyse significantly into the free alcohol and acid.

STATEMENT OF INVENTION

Accordingly, the invention provides oral composition comprising:

(a) an alkyl hydroxybenzoate represented by formula 1

Formula 1:

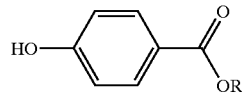

wherein R represents an alkyl group comprising at least five carbon atoms, and (b) said composition having an alkaline pH.

DESCRIPTION OF INVENTION

The alkyl group of the compound according to Formula 1 is an alkyl comprising more than five carbon atoms. Preferably, the alkyl group comprises no more than 30 carbon atoms. More preferably the alkyl group comprises from 6 to 15 carbon atoms, especially from 6 to 10 and especially preferably, 7 or 8. These longer chain alkyl parahydroxy benzoic acids have never been considered before in alkaline environments because they were thought to be unstable.

Further, the alkyl group may be branched or straight chain and/or substituted or unsubstituted.

Preferred alkyl groups include octyl, heptyl and 2-ethylhexyl, more preferably, n-octyl or 2-ethylhexyl. Such compounds may be made by simple esterification of 4-hydroxybenzoic acid with the respective alcohol. Such a process is a simple step for the person skilled in the art to carry out.

The most preferred alkyl groups on the alkyl para hydroxybenzoic acids are straight chain and include seven or, more preferably, eight carbon atoms.

The compound according to Formula 1 is preferably present in an amount such that an antibacterial effect can be provided. In practice this ranges from 0.15 to 20% by weight of the composition according to the invention. Preferably, in an amount ranging from 0.8 to 10% by weight and even more suitably from 1.0 to 3% by weight.

This surprising stability is particularly suitable for the longer chain alkyl parahydroxybenzoates, for example where the alkyl chain comprises at least seven carbons, especially preferably eight carbons in a straight chain and without wishing to be bound by theory it is thought that the longer chain parabens agglomerate to form micelles within the composition structure and thus protect each other from degradation in the alkaline environment. This effect is particularly surprising where chalk is used as an abrasive and the pH of the composition is thus much raised, from 8.5 to 11.5 being typical.

The oral composition according to the invention has an alkaline pH. This means that the pH of the composition is more than 7. Preferably, the pH of the composition is from 7.5 to 12, more preferably from 8 to 11, especially preferably from 9 to 10. It is to be understood that any combination of any given bottom range limit with any given top limit can be used.

The oral composition according to the invention may comprise chalk as abrasive. Typically the term chalk is denoted to mean not just pure calcium carbonate but also ground marble. Chalk is usually in a crystallised form with many different types of crystals. For example, aragonite and calcite are two common crystal types. Further, natural chalk may also be used in oral care compositions. This natural chalk is commonly referred to as fine ground natural chalk or FGNC.

Where FGNC is used it typically comprises particulate material of number average diameter ranging from 1 to 15 μm, preferably from 2 to 10 μm.

The chalk of the composition may even comprise a mixture of chalk types, e.g. precipitated calcium carbonate (PCC) plus FGNC, or even different types of FGNC.

Typically the amount of chalk present when used as an abrasive ranges from 1 to 60% by weight of the composition, preferably from 20 to 50% by weight.

It is to be understood that the oral composition according to the invention is capable of being used to clean the oral cavity, whether as part of a quotidian regime or as part of a one-off treatment. Typically oral care compositions comprise orally acceptable carriers. Further, oral compositions usually comprise oral care benefit agents selected from the group consisting of anti-caries agents, anti-tartar agents, flavours, whitening agents, abrasives, bleaches and anti-malodour agents.

The oral composition according to the invention may also comprise bicarbonate as abrasive.

In another preferred embodiment the composition according to the invention comprises a surfactant. The surfactant is selected from the group consisting of anionic, non-ionic, cationic and zwitterionic surfactants or mixtures thereof and is present in the composition in an amount ranging from 0.01 to 5% by weight, preferably from 0.1 to 2.5% by weight and especially preferably from 0.5 to 1.8% by weight of the composition. Preferred surfactants include the anionic surfactants, in particular the alkali-metal alkyl sulphates, e.g. sodium lauryl sulphate.

The oral composition according to the invention may also comprise further ingredients which are common in the art, such as:

antimicrobial agents, e.g. Triclosan, chlorhexidine,
   copper-, zinc- and stannous salts such as zinc citrate,
   zinc sulphate, zinc glycinate, sodium zinc citrate and
   stannous pyrophosphate, sanguinarine extract,
   metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates;

vitamins such as Vitamins A, C and E; plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.;

flavours, e.g. peppermint and spearmint oils;

proteinaceous materials such as collagen;

preservatives;

opacifying agents;

colouring agents;

pH-adjusting agents;

sweetening agents;

pharmaceutically acceptable carriers, e.g. starch, sucrose, water or water/alcohol systems etc.;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition;

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included;

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

The oral compositions may be in any form common in the art, e.g. toothpaste, gel, mousse, aerosol, gum, lozenge, powder, cream, etc. and may also be formulated into systems for use in dual-compartment type dispensers.

Embodiments according to the invention shall now be discussed with reference to the following non-limiting examples.

EXAMPLE

The following formulation is a composition according to the invention and is made by ordinary methods known to a skilled person.

| Ingredient | w/w % |
|---|---|
| Fine ground natural chalk | 40 |
| Sorbitol (70% aq) | 25 |
| Sodium lauryl sulphate | 2.5 |
| sodium monofluorophosphate | 1.1 |
| octyl parahydroxybenzoic acid | 1.0 |
| sodium carboxy methyl cellulose | 0.9 |
| trisodium phosphate | 0.3 |
| flavour | 1 |
| water | to 100 |

This octyl parahydroxy benzoic acid in this formulation was stable at 37° C. for two months.

What is claimed is:

1. Oral dental care composition comprising 0.15 to 20% of weight of (a) an alkyl hydroxybenzoate represented by formula 1

Formula 1:

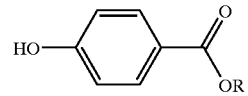

wherein R represents an alkyl group comprising at least five carbon atoms, and (b) said composition having an alkaline pH and stable at 37° C. for two months.

2. Composition according to claim 1, wherein R represents an alkyl group comprising from six to fifteen carbon atoms.

3. Composition according to claim 1, wherein R represents an alkyl group comprising from seven to ten carbon atoms.

4. Composition according to claims 1, wherein R represents a group selected from the group consisting of octyl and heptyl.

5. Composition according to claim 1, wherein R represents a branched alkyl group.

6. Composition according to claim 1, wherein R is a straight chain alkyl group.

7. Composition according to claim 1, wherein R is 2-ethylhexyl.

8. Composition according to claim 1, wherein the composition is an oral composition and comprises an orally acceptable carrier.

9. Composition according to claim 1, wherein the composition is selected from the group consisting of pastes, gels, foams, liquids, powders and chewing gums and is suitable for use in dental care.

10. Composition according to claim 1, wherein the pH of the composition is from 7.5 to 12.

11. Composition according to claim 1, wherein the pH of the composition is from 8 to 11.

12. Composition according to claim 1, wherein the pH of the composition is from 9 to 10.

13. Composition according to claim 1, wherein the composition comprises chalk as abrasive.

14. Composition according to claim 1 comprising a bicarbonate.

* * * * *